United States Patent [19]

Kaasgaard et al.

[11] Patent Number: 5,525,483

[45] Date of Patent: Jun. 11, 1996

[54] PROCESS FOR PREPARATION OF β-LACTAMS UTILIZING A COMBINED CONCENTRATION OF ACYLATING AGENT PLUS β-LACTAM DERIVATIVE OF AT LEAST 400 MM

[75] Inventors: Svend G. Kaasgaard, Soeborg; Ulla Veitland, Bagsvaerd, both of Denmark

[73] Assignee: Gist Brocades B.V., Netherlands

[21] Appl. No.: 182,872

[22] Filed: Jan. 18, 1994

Related U.S. Application Data

[63] Continuation of Ser. No. 955,907, Dec. 16, 1992, abandoned.

[30] Foreign Application Priority Data

Jul. 4, 1990 [EP] European Pat. Off. ............... 90610045

[51] Int. Cl.$^6$ ............................. C12P 37/04; C12P 37/02
[52] U.S. Cl. .................................. 435/45; 435/46; 435/50
[58] Field of Search ................................ 435/45, 46, 50

[56] References Cited

U.S. PATENT DOCUMENTS

| | | | |
|---|---|---|---|
| 3,079,305 | 2/1963 | Kaufmann et al. | 435/45 |
| 3,152,050 | 10/1964 | Grant et al. | 435/45 |
| 4,335,211 | 6/1982 | Hashimoto et al. | 435/50 |

FOREIGN PATENT DOCUMENTS 3507403  9/1986  Germany.

*Primary Examiner*—Herbert J. Lilling
*Attorney, Agent, or Firm*—Bierman and Muserlian

[57] ABSTRACT

β-Lactam derivatives are synthesized by an enzymatic reaction of the parent amino β-lactam with the corresponding acylating agent, the concentration of the acylating agent plus the concentration of β-lactam derivative in the reaction mixture being above about 400 mM.

39 Claims, No Drawings

PROCESS FOR PREPARATION OF β-LACTAMS UTILIZING A COMBINED CONCENTRATION OF ACYLATING AGENT PLUS β-LACTAM DERIVATIVE OF AT LEAST 400 MM

STATUS OF RELATED APPLICATIONS

This application is a continuation of Ser. No. 07/955,907, filed Dec. 16, 1992, now abandoned.

TECHNICAL FIELD

This invention relates to a process for the preparation of β-lactam derivatives by enzymatic acylation of the parent amino β-lactam with an acylating agent. The amino β-lactam may be 6-aminopenicillanic acid (6-APA), 7-aminodesacetoxycephalosporanic acid (7-ADCA), 7-aminocephalosporanic acid (7-ACA) or 7-amino-3-chloro-3-cephem-4-carboxylate and the acylating agent may be a derivative of D-phenylglycine or D-p-hydroxyphenylglycine.

BACKGROUND ART

Today, semisynthetic β-lactams such as Ampicillin, Amoxicillin, Cefaclor, Cephalexin, Cephadroxil and Cephaloglycin are prepared in industry by chemical methods, for example by reacting an amino β-lactam such as 6-aminopenicillanic acid, usually having its carboxyl group protected, with an activated side chain derivative, followed by the removal of the protecting group by hydrolysis. It is important due to, for example, yield, that the amino β-lactam, for example 6-APA, is used in a pure, dry form, preferably in a purity higher than 97%. For example, Ampicillin (6-D-α-aminophenylacetamidopenicillanic acid) can be prepared by reacting 6-APA, having a..suitable protected carboxyl group, with D-phenylglycine acidchloride, followed by removal of the protecting group by hydrolysis. These reactions typically involve costly steps such as sub zero degree Celcius conditions and organic solvents like methylene chloride and silylation reagents.

Enzymatic production of Ampicillin from pure 6-APA and a D-phenylglycine derivative (such as a lower alkyl ester) is known from West German patent application having publication No. 2,163,792, Austrian Patent No. 243,986, Dutch patent application No. 70-09138, West German patent application having publication No. 2,621,618 and European patent application having publication No. 339,751. Processes described in the prior art have typically used below 50 mM of the D-phenylglycine derivative and below 25 mM of 6-APA, the highest yield reported was 88% (European patent application having publication No. 339,751).

The amino β-lactam such as 6-APA is commonly produced by enzymatic hydrolysis of a fermented -penicillin (for example penicillin V or penicillin G) followed by removal of the liberated side chain (phenoxyacetic acid etc.). Besides impurities originating from the fermentation, the resulting crude solution typically contains the amino β-lactam at a concentration of 150–200 mM. The crude solution can be purified and crystallized to obtain pure 6-APA or 7-ADCA (in the 7-ADCA case, the fermented penicillin have been through another process before the hydrolysis step)..

The potential drawbacks of the known enzymatic methods for production of Ampicillin, Amoxicillin and Cephalexin (none have yet been upscaled to industrial applicability) are the high costs (yield losses) and investments due to the necessary unit operations incurred when the amino β-lactam is isolated, purified and dried before being used as raw material for the reaction leading to a semisynthetic β-lactam. Furthermore, the starting concentrations of the 6-APA are very low (typically less than 50 mM), thus making the isolation of the formed Ampicillin more difficult and thus more costly. Also, a higher yield in the enzymatic formation of Ampicillin is desirable.

A process for enzymatic synthesis of Amoxicillin is described in *Agric. Biol. Chem.* 44 (1980), 821 et seq., which process is performed in a reaction medium containing 2.5% (volume/volume) or more of 2-propanol and 5% (volume/volume) of other alcohols. When one of the last mentioned alcohols or 2.5% of 2-propanol are used, the initial concentration of the starting materials, D-α-(p-hydroxyphenyl)glycine methyl ester and 6-aminopenicillanic acid, is very low, i.e. 100 and 50 mM, respectively. When 5% of 2-propanol is used, the-initial concentration of the starting materials, D-α-(p-hydroxyphenyl)glycine methyl ester and 6-aminopenicillanic acid, is 460 and 230 mM, respectively. It is stated in this paper that the addition of more than 100 mM of D-α-(p-hydroxyphenyl)glycine methyl ester and of more than 50 mM of 6-aminopenicillanic acid markedly suppressed the ration of conversion of 6-aminopenicillanic acid into amoxicillin. The conclusion of this statement is that this publication teaches away for increasing the concentration of the amino β-lactam and of the acylating agent in the reaction mixture.

After the effective filing date of the application for a patent on this invention, namely Sep. 18–21, 1990, a poster was published at a NATO Workshop. The poster dealt with the preparation of cephalosporins and, according to this poster, working at low temperature had several positive effects on the reaction. The highest concentration of acylating agent used by this work was 355 mM of D-α-phenylglycine methyl ester and there was no indication on the poster according to which it could be advantageous to use a higher concentration of the acylating agent.

STATEMENT OF THIS INVENTION

It has now, surprisingly, been found that the yield in the enzymatic preparation of β-lactam derivatives can be improved by carrying out the reaction at high concentrations of the acylating agent.

Herein the terms amino β-lactam, acylating agent and β-lactam derivative cover the two starting materials, respectively, and the resulting product relating to the process of this invention. Hence, the process of this invention can be illustrated by the following reaction scheme:

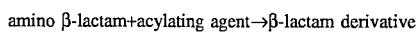

amino β-lactam+acylating agent→β-lactam derivative

The β-lactam derivative has a substantially higher antibiotic activity than the amino β-lactam. The amino β-lactam has a free amino group which is acylated by the reaction according to this invention. The acylating agent may be in the free acid form or may be in an activated form such as amides or esters. Herein the term β-lactam nucleus comprises both the amino β-lactam and the β-lactam derivative. The concentration of β-lactam nucleus stated hereinafter is thus the concentration of amino β-lactam plus the concentration of β-lactam derivative.

It is an important feature of the process of this invention that the concentration of the acylating agent plus the concentration of the β-lactam derivative in the reaction mixture is above 400 mM. One way of obtaining this concentration in the reaction mixture is by adding, in a batchwise process, the acylating agent to the reaction mixture in an amount sufficient to give an initial concentration of the acylating agent in the reaction mixture of more than about 400 mM.

By the process of this invention, it is possible and attractive to use a crude solution of the amino β-lactam, for example 6-APA or 7-ADCA, without dilution. Loss of the amino β-lactam, for example 6-APA or 7-ADCA, during purification and/or isolation steps is thus avoided, and investments in purification equipment for, for example, Ampicillin, Amoxicillin and Cephalexin are thus minimized as purification equipment former used for isolation of 6-APA now can be used for isolation of Ampicillin, Amoxicillin and Cephalexin.

Advantageously, the high yield according to this invention can be obtained without the need for low temperatures and organic solvents as methylene chloride. Thus, 96% yield of Ampicillin was obtained at 20° C.

Accordingly, this invention provides a process for enzymatic reaction of an amino β-lactam, for example, 6-aminopenicillanic acid, 7-aminodesacetoxycephalosporanic acid, 7-aminocephalosporanic acid or 7-amino-3-chloro-3-cephem- 4-carboxylate, with an acylating agent, for example, a derivative of D-phenylglycine or D-p-hydroxyphenylglycine.

In one aspect, this process is characterized in that the concentration of the starting amino β-lactam in the reaction mixture is in the range from about 50 to about 750 mM, preferably above about 100 mM, more preferred above about 150 mM, most preferred above about 200 mM. In another aspect, this process is characterized in that the initial concentration of the starting amino β-lactam in the reaction mixture is in the range from about 50 to about 750 mM, preferably above about 100 mM, more preferred above about 150 mM, most preferred above about 200 mM. In a still further aspect, this process is characterized in that the initial amount of the acylating agent, for example, the D-phenylglycine or D-p-hydroxyphenylglycine derivative, in the reaction mixture-is above the solubility of said agent in the reaction mixture (preferably at least 50% above the solubility); or the initial amount of the acylating agent in the reaction mixture is above half of the solubility of said acylating agent plus the initial amount of the amino β-lactam in the reaction mixture (preferably above the solubility of the acylating agent in the reaction mixture+the initial amount of the amino β-lactam). In a still further aspect, this invention relates to a process whereby the concentration of acylating agent plus the concentration of β-lactam derivative in the reaction mixture is above about 450 mM, preferably above about 500 mM, more preferred above about 650 mM, even more preferred above about 700 mM). In an additional aspect, this invention relates to a process whereby the initial concentration of acylating agent in the reaction mixture is above about 450 mM, preferably above about 500 mM, more preferred above about 650 mM, even more preferred above about 700 mM.

The advantages of this invention are, inter alia, as follows:

1) The use of an organic solvent such as methylene chloride is omitted which avoids pollution.

2) The use of silylating agents is avoided.

3) The use of extraction at low temperature such as 0° C. can be omitted.

4) The high concentration of reactants is an advantage for the following purification.

5) The resulting β-lactam derivative has a high purity not yet seen on the commercial bulk market.

6) The content of byproducts in the reaction mixture is very low.

7) Compared with the chemical synthesis, fewer steps are used.

DETAILED DESCRIPTION OF THIS INVENTION

Examples of β-lactam derivatives that may be produced by the process of this invention are Ampicillin, Amoxicillin, Cefaclor, Cephalexin, Cephadroxil.

The acylating agent may be a derivative of D-phenylglycine or D-p-hydroxyphenylglycine such as a lower alkyl (methyl, ethyl, n-propyl or isopropyl) ester or an amide which is unsubstituted in the —$CONH_2$ group. The amide is preferred. The derivative may be used in the form of a salt, for example, the HCl salt or the $H_2SO_4$ salt. The acylating agent may be added in an active form or the active form may be formed in situ.

The enzyme to be used in the process of this invention may be any enzyme catalyzing the reaction in question. Such enzymes have been known since around 1966. Enzymes to be used are, for example, termed penicillin amidase or penicillin acylase and classified as E.C. 3.5.1.11. A number of microbial enzymes are known to have this activity, derived from for example Acetobacter, Xanthomonas, Mycoplana, Protaminobacter, Aeromonas (West German patent application having publication No. 2,163,792) Pseudomonas (Austrian Patent No. 243986), Flavobacterium (Dutch patent application No. 70-09138), Aphanocladium, Cephalosporium (West German patent application having publication No. 2,621,618), *Acetobacter pasteurianum, Bacillus megaterium, Xanthomonas citrii* (European patent application having publication No. 339,751), *Kluyvera citrophila* (*Agr. Biol. Chem.* 37 (1973), 2797–2804) and *Escherichia coli* (West German patent application having publication No. 2,930,794). The *Escherichia coli* enzyme is commercially available. The enzyme also may be a so-called ampicillin hydrolase, acylase or amidase. In this connection, reference is, inter alia, made to *Hakko to Kogyo* 38 (1980), 216 et seq., the content of which is incorporated by reference. >

It is preferred to use the enzyme in a reuseable form, for example, in entrapped or immobilized form. Immobilization may be done by any known method. Immobilized *Escherichia coli* enzyme is commercially available from Boehringer Mannheim GmbH, Germany, under the trade name Enzygel.

The process of this invention is generally carried out in a system containing water. If desired, an organic solvent may be added.

The solubility of the acylating agent such as the D-phenylglycine or D-p-hydroxyphenylglycine derivative will vary with the identity of the derivative and with the composition of the reaction medium. In an aqueous system as used in the examples, the solubility of the HCl salt of D-phenylglycine amide is typically approximately 450 mM. However, the solubility is very dependent on the salt components in the solution, as well as on the pH value and the temperature of the solution. In some embodiments of the process of this invention, the initial reaction mixture is a slurry containing undissolved acylating agent and/or β-lactam, which will dissolve partly or fully during the course of the reaction. The β-lactam formed may precipitate during the reaction and, also, the hydrolysis products of the acylating agent such as D-phenylglycine and D-p-hydroxyphenylglycine, may precipitate. Hence, in many cases the reaction mixture will be a slurry throughout the reaction.

The amino β-lactam, for example 6-APA or 7-ADCA, used in the process of this invention may be obtained by enzymatic hydrolysis of the fermented penicillins or cephalosporins, (for example penicillin V, penicillin G or cephalosporin C) or their ring enlarged analogues (for example V-DCA and G-DCA) or derivatives thereof followed by removal of the hydrolysis by-product, if desired (phenoxyacetic acid etc.). Advantageously, the crude solution can be used directly without further purification or dilution.

Generally, the reaction temperature of the process of this invention may vary between about 0° C. and about 35° C., is especially between about 10° C. and about 30° C. Temperatures in the range about 20°–30° C. may be preferred for convenient operation. The suitable pH value depends on the type and purity of enzyme. Using *Escherichia coli* enzyme, the pH value is typically in the range from about 5.5 through about 7.5, preferably in the range from about 6.1 through about 7. For the preparation of Amoxicillin, a pH value in the range from about 5.5 through about 6.4 is preferred. Control of the pH value may be used. Suitable reaction times are from several minutes to several hours, in particular from about ½ hour to about 8 hours. Suitable enzyme concentrations may be from about 1 U/ml to about 100 U/ml (1 U=one unit of enzyme activity, see below).

Using the process according to this invention, extraordinary high yields can be obtained. The high yields are obtained using the teachings of this invention and properly selecting the concentration of the acylating agent, the ratio between the concentration of acylating agent and the starting amino β-lactam, the pH value and the enzyme.

Recovery and purification of the product can be achieved by methods known per se, for example by crystallisation.

DEFINITIONS AND METHODS OF ANALYSIS

Enzyme activity

As definition of penicillin G acylase activity the following is used: one unit (U) corresponds to the amount of enzyme that hydrolyses per minute 1 μmole penicillin G under standard conditions (5% penicillin G, 0.2M Sodium phosphate buffer, pH value 8.0, 28° C.).

HPLC analysis of reaction components:

Column: RP LC-18, (250×4.6 mm; 5 μm)

Eluent A: 25 mM Phosphate buffer, pH value 6.5

Eluent B: acetonitrile

Gradient:

| Time, minutes | eluent B, % |
|---|---|
| 0 → 10 | 1 → 20 |
| 10 → 20 | 20 |

Flow: 1 ml/min. Detection: 215 nm.

Retention times in minutes: 4.1 (D-PG); 6.3 (7-ADCA); 8.1 (6-APA); 9.1 (D-PGA); 13.4 (Cephalexin); 13.9 (Ampicillin); 18 (D-PGM).

HPLC analysis of Amoxicillin.

Column: RP LC-18, 5 μm, (250×4.6 mm)

Solvent: 5% acetonitrile in 25 mM phosphate buffer, pH value: 6.5. Flow: 1 ml/min. UV-detection at 215 nm.

Retention times in minutes: 2.5 (D-p-hydroxyphenylglycine); 3.3 (HPGA); 5.4 (6-APA); 13.2 (Amoxicillin).

This invention is further illustrated by the following examples which, however, are not to be construed as limiting the scope of protection.

EXAMPLE 1

Enzymatic synthesis of Ampicillin.

A solution of 100 mM 6-APA and D-PGA in a concentration as indicated in table 1 is adjusted to pH value 6.4 and equilibrated at 20° C. and 345 U soluble enzyme from *Escherichia coli*, supplied from Gesellschaft für Biotechnologische Forschung GmbH, Braunschweig, Germany, is added, (total volume: 20 ml).

The synthesis is carried out at 25° C. and at pH-stat conditions. The maximum yields, based upon HPLC analysis are shown in table 1.

TABLE 1

| mM D-PGA | maximum yield of Ampicillin, % | reaction time, hours |
|---|---|---|
| 270 | 74 | 9 |
| 750 | 98 | 24 |

EXAMPLE 2

Enzymatic synthesis of Cephalexin.

Same as described in Example 1, only 100 mM 7-ADCA is used instead of 6-APA. Under these conditions Cephalexin is obtained and the max. yields obtained at different concentrations of D-PGA·HCl are shown in table 2.

TABLE 2

| mM D-PGA HCl | maximum yield of Cephalexin, % |
|---|---|
| 300 | 65 |
| 700 | 92 |

EXAMPLE 3 pH dependence.

250 mM 6-APA and 700 mM D-PGA sulphate salt are adjusted to a pH value as indicated in table 3, and the enzymatic synthesis is carried out at 20° C. and pH stat-conditions, total volume 20 ml and 700 U soluble enzyme from *Escherichia coli*.

TABLE 3

| pH value | maximum yield, % | reaction time, hours |
|---|---|---|
| 3 | 60 | 48 |
| 6.4 | 94 | 21 |
| 7.0 | 93 | 3 |

EXAMPLE 4

Temperature dependence

Starting with 180 mM 6-APA and 700 mM D-PGA at pH value 6.4 and 600 U soluble enzyme from *Escherichia coli* (total volume: 20 ml) and running the synthesis at temperatures as indicated in Table 4, the maximal yields of Ampicillin obtained are shown in Table 4.

TABLE 4

| Temperature, °C. | maximum yield, % | reaction time, hours |
| --- | --- | --- |
| 10 | 95 | 72 |
| 20 | 96 | 22 |
| 35 | 60 | 4 |

EXAMPLE 5

This example was performed analagously with Example 1 using D-PGM instead of D-PGA. The maximum yields of Ampicillin obtained are as stated in Table 5.

TABLE 5

| D-PGM, mM | Ampicillin formed, % | reaction time, hours |
| --- | --- | --- |
| 270 | 74 | 12 |
| 700 | 86 | 25 |

EXAMPLE 6

Pen V partly purified from fermentation broth by filtration, extraction into butyl acetate and back into an aqueous phase resulting in a solution of 10 % (weight/volume) pen V is hydrolysed by Semacylase™ (immobilized pen V acylase from Novo Nordisk A/S) at a pH value of 7.0. The phenoxyacetic acid is removed by extraction and to the resulting 6-APA (150 mM) solution, containing minor amounts of biproducts from degraded pen V and 6-APA, is added 45 U/ml soluble enzyme from Escherichia coli and D-PGA (to a final Concentration of 700 mM). The pH value is adjusted to 6.4 and the reaction is allowed to proceed at 25° C. keeping the pH value constant.

Under these conditions a total of 135 mmole of Ampicillin (90%) is formed per liter of reaction volume.

EXAMPLE 7

Use of immobilized pen G acylase from Boehringer Mannheim 500 mg of immobilized enzyme is suspended ad 10 ml with water. The enzyme solution was mixed with a solution of 6-APA and D-PGA to a total volume of 25 ml the resulting mixture containing 230 mM 6-APA and 920 mM D-PGA, having pH value 6.4 and equilibrated at room temperature. The synthesis reaction was allowed to proceed at pH stat conditions for 22 hours after which 91% of the 6-APA was converted to Ampicillin.

EXAMPLE 8

Enzymatic synthesis of Amoxicillin.

A mixture of 968 mg 6-APA and 3718 mg HPGA in water is adjusted to pH 6.2 at 15° C. and 1656 U soluble penicillin G acylase from *E. coli* is added to a final volume of 29.8 ml. The synthesis is allowed to proceed at constant temperature, using 2M sulfuric acid to keep the pH at 6.2. After 27.3 hours the reaction mixture contained 136.6 mM Amoxicillin, corresponding to a yield of 91% based on the 6-APA consumption.

EXAMPLE 9

Enzymatic synthesis of Amoxicillin.

1656 U soluble penicillin G acylase from *E. coli* is added to a mixture of 6-APA and HPGA (200 mM and 750 mM final concentration, respectively) in water at pH 6.0 and 30° C. After reacting for 9 hours keeping the temperature and pH constant using 2M sulfuric acid for the titration, 190 mM Amoxicillin was produced (95% yield) based on HPLC-analysis.

EXAMPLE 10

Enzymatic synthesis of Amoxicillin.

Starting with 150 mM 6-APA, 600 mM HPGA, 1656 U soluble penicillin G acylase from *E. coli*, 140 mM Amoxicillin (93%) was produced after 8 hours, when the reaction was carried out at pH 5.7 and at 35° C.

EXAMPLE 11

Enzymatic synthesis of Amoxicillin.

Same conditions as described in example 9, using 200 mM 6-APA and 450 mM HPGA resulted in 91% conversion of the 6-APA to Amoxicillin after 9 hours.

Abbreviations

6-APA is 6-aminopenicillanic acid, 7-ADCA is 7-aminodesacetoxycephalosporanic acid, D-PGA is D-phenylglycinamide, DPGM is D-phenylglycin methyl ester, V-DCA is 7-phenoxyacetamidodesacetoxycephalosporanic acid, G-DCA is 7-phenylacetamidodesacetoxycephalosporanic acid and HPGA is D-p-hydroxyphenylglycinamide.

We claim:

1. In the process for the preparation of a β-lactam amide comprising subjecting a member selected from the group consisting of a penicillin, 7-aminodesacetoxycephalosporanic acid, 7-aminocephalosporanic acid and 7-amino-3-chloro-3-cephem-4-carboxylate to an enzymatic reaction with an acylating agent in a reaction mixture containing less than 5% (volume/volume) of 2-butanol if the β-lactam amide is amoxicillin and the acylating agent is D-α-(p-hydroxy-phenyl) glycine methyl ester, the improvement comprising using a concentration of the acylating agent and the β-lactam amide in the reaction mixture greater than 400 mM and the enzyme is derived from a microorganism selected from the group consisting of *Escherichia coli, Acetobacter pasteurianum, Xanthomonas citrii, Kluyvera citrophila,* or *Bacillus megaterium.*

2. The process of claim 1 wherein the temperature of the reaction is less than 35° C.

3. A process according to claim 1, wherein the temperature is below about 30° C.

4. A process according to claim 1, wherein the temperature is below about 30° C.

5. A process according to claim 1 or 2, wherein the reaction mixture contains less than about 2.5% (volume/volume) of 2-butanol.

6. A process according to claim 1 or 2, wherein the amino β-lactam is 6-aminopenicillanic acid, 7-aminodesacetoxycephalosporanic acid, 7-aminocephalosporanic acid or 7-amino-3 chloro-3-cephem-4-carboxylate.

7. A process according to claim 1 or 2, wherein the acylating agent is D-phenylglycine or D-p-hydroxyphenylglycine or derivatives thereof.

8. A process according to claim 1 or 2, wherein the β-lactam derivative is ampicillin, amoxicillin, cefaclor, cephalexin, or cephadroxil.

9. A process according to claim 1 or 2, wherein the concentration of the amino β-lactam in the reaction mixture is in the range from about 50 to about 750 mM.

10. A process according to claim 1 or 2, wherein the concentration of the amino β-lactam in the reaction mixture is above about 100 mM.

11. A process according to claim 1 or 2, wherein the concentration of the amino β-lactam in the reaction mixture is above about 150 mM.

12. A process according to claim 1 or 2, wherein the concentration of the amino β-lactam in the reaction mixture is above about 200 mM.

13. A process according to claim 1 or 2, wherein the concentration of the amino β-lactam in the reaction mixture when the enzymatic reaction starts is in the range from about 50 to about 750 mM, 14. A process according to claim 1 or 2, wherein the concentration of the acylating agent plus the concentration of β-lactam derivative in the reaction mixture is above about 450 mM.

15. A process according to claim 14, wherein the resulting β-lactam derivative is amoxicillin.

16. A process according to claim 1 or 2, wherein the concentration of acylating agent in the reaction mixture when the enzymatic reaction starts is greater than 450 mM.

17. A process according to claim 16, wherein the β-lactam derivative is amoxicillin.

18. A process according to claim 16, wherein the concentration of the acylating agent plus the concentration of β-lactam derivative is above about 500 mM.

19. A process according to claim 16, wherein the concentration is above about 650 mM.

20. A process according to claim 16, wherein the concentration is above about 700 mM.

21. A process according to claim 16, wherein the concentration of the acylating agent in the reaction mixture when the enzymatic reaction starts is greater than 700 mM.

22. A process according claim 1 or 2, wherein the reaction is performed at a temperature in the range from about 0° to about 35° C.

23. A process according to claim 1 or 2, wherein the temperature is above about 10° C.

24. A process according to claim 1 or 2, wherein the reaction is performed at a pH value in the range from above about 5 through about 7.

25. A process according to claim 1 or 2, wherein the amino β-lactam is prepared by hydrolysis of penicillin V, penicillin G, 7-phenoxyacetamidodesacetoxycephalosporanic acid (V-DCA), 7-phenylacetamidodesacetoxycephalosporanic acid (G-DCA), or cephalosporin C or a derivative thereof.

26. A process according to claim 25, which comprises the further step of removal of a side chain liberated by hydrolysis.

27. A process according to claim 1 or 2, wherein the amount of the acylating agent in the reaction mixture when the enzymatic reaction starts is above the solubility of the agent in the reaction mixture.

28. A process according to claim 1 or 2, wherein the amount of the acylating agent in the starting reaction mixture is greater than half the amount of said agent which is soluble in the reaction mixture plus the amount of the amino β-lactam in the reaction mixture when the enzymatic reaction starts.

29. A process according to claim 28, wherein the amount of the acylating agent in the reaction mixture is greater than the amount of the agent which is soluble in the reaction mixture plus the amount of the amino β-lactam in the starting reaction mixture.

30. A process according to claim 1 or 2, wherein the acylating agent is an amide acylating agent, or an ester acylating agent, which ester acylating agent contains 1–3 carbon atoms in its ester moiety.

31. A process according to claim 1 or 2, wherein the acylating agent is an amide.

32. A process according to claim 1 or 2, wherein the —$CONH_2$ group is unsubstituted.

33. A process according to claim 1 or 2, wherein the enzyme used is classified as EC 3.5.1.11.

34. A process according to claim 1 or 2, wherein the enzyme used is able to hydrolyze penicillin G or ampicillin.

35. A process according to claim 1 or 2, wherein an enzyme in reusable form is used.

36. A process according to claim 1 or 2, wherein the enzymatic reaction is carried out in an aqueous system.

37. A process according to claim 36, wherein the reaction is carried out in the presence of an organic solvent.

38. A process according to claim 1 or 2, wherein the yield of the resulting β-lactam derivative is at least about 90% (mol/mol), based upon the total amount of β-lactam nucleus.

39. A process according to claim 38, wherein the yield is at least about 95% (mol/mol).

* * * * *